July 27, 1954 J. DE VINK Plant Pat. 1,293
ROSE PLANT
Filed July 20, 1953
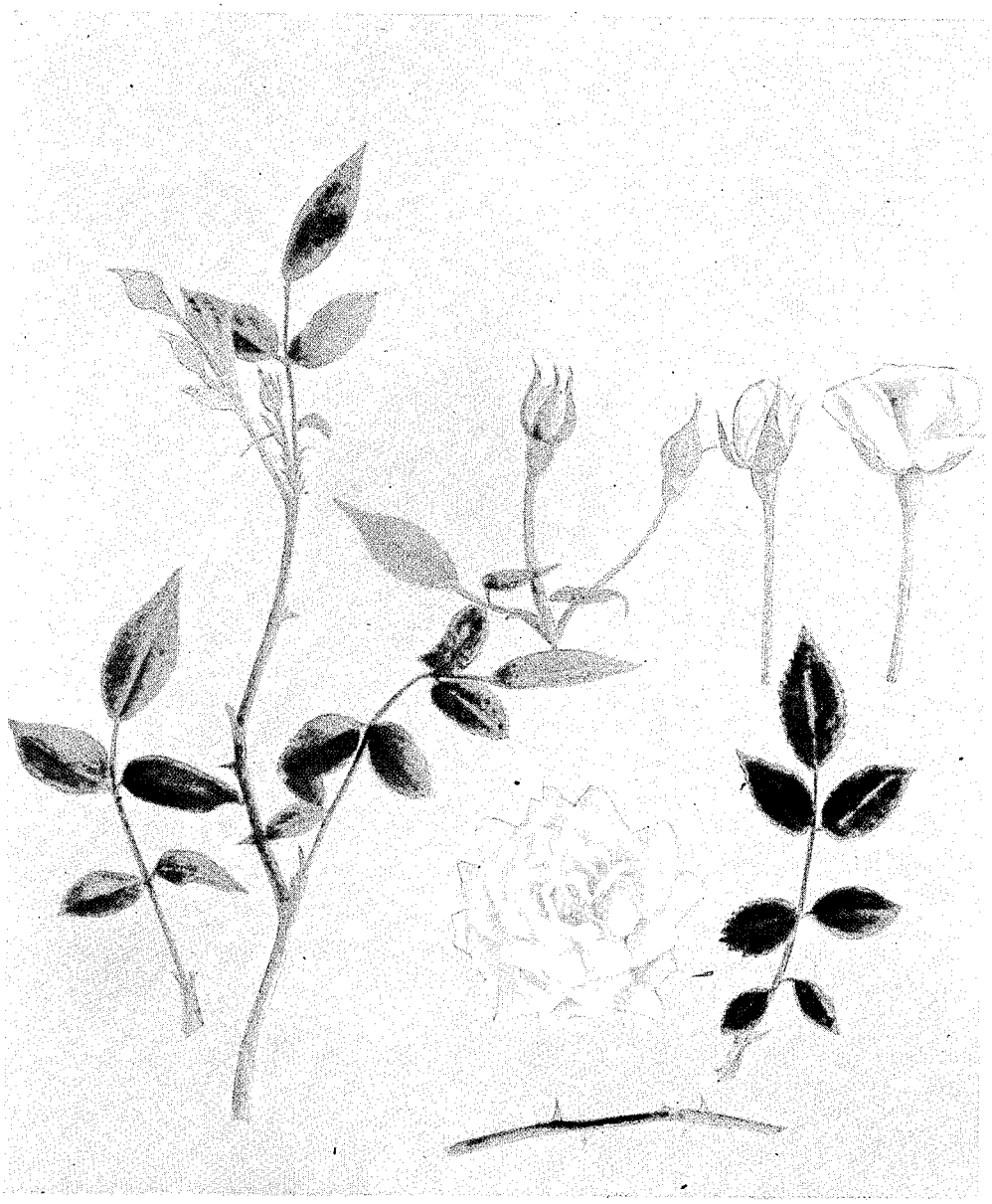
Inventor.
John de Vink
By: Robb & Robb
Attorneys.

Patented July 27, 1954

Plant Pat. 1,293

UNITED STATES PATENT OFFICE 1,293

ROSE PLANT

John de Vink, Boskoop, Netherlands, assignor to The Conard-Pyle Company, West Grove, Pa., a corporation of Pennsylvania Application July 20, 1953, Serial No. 369,265

1 Claim. (Cl. 47—61)

The present invention relates to a new and distinct variety of rose plant of the miniature class, which was originated by me by crossing the variety "Ellen Poulsen" (unpatented) with the variety "Tom Thumb" (Plant Patent No. 169).

As a result of this breeding, I have created a new variety of rose plant which is a true miniature, and which is primarily distinguished from its parents, as well as from all other varieties of its class, by the distinctive, bright Pink general color tonality of its flowers, this color being a new color in the class of miniature roses.

Asexual reproduction of my new variety by cuttings at West Grove, Pennsylvania, U. S. A., shows that the foregoing characteristics and distinctions come true to form and are established and transmitted through succeeding propagations.

The accompanying drawing shows typical specimens of the flowers, foliage and stems of my new variety in different stages of development, the same being depicted in color as nearly true as it is reasonably possible to make the same in a color illustration of this character.

The following is a detailed description of my new variety, with color terminology in accordance with Ridgway's Color Standards and Nomenclature, except where general terms of ordinary dictionary significance are obvious:

Type: Hardy; dwarf; greenhouse and outdoor; for cut flowers and for garden decoration.
Class: Miniature.
Breeding: Seedling.
*Seed parent.*—"Ellen Poulsen."
*Pollen parent.*—"Tom Thumb."
Propagation: Holds its distinguishing characteristics through succeeding propagations by cuttings.

*Flower*

Locality where grown and observed: West Grove, Pennsylvania, U. S. A.
Flowers borne: Several to stem; in irregular cluster; on normal strength, medium length stems.
Quantity of bloom: Free, both outdoors and in greenhouse.
Continuity: Continuous.
Fragrance: Practically none.
Bud:
*Peduncle.*—Long; medium caliper; erect; smooth; with few brown hairs. Color—medium green.
*Before calyx breaks.*—Size—small. Form—medium length; ovoid; with foliaceous appendages on the surface of the bud; with entire foliaceous parts extending beyond the tip of the bud equal to ¼ of its length.
*As calyx breaks.*—Color—Amaranth Purple, Plate XII.
*As first petal opens.*—Size—medium for a miniature. Form—medium long; cup-shaped. Color: outside—Rose Color, Plate XII, with Chrysolite Green, Plate XXXI at base; inside—Tyrian Rose, Plate XII, with Lumiere Green, Plate XVII at base.
*Opening.*—Opens up well.

Bloom:
*Size (when fully open).*—Medium-large for a miniature; about 1¼ inches in diameter.
*Petalage.*—Very double; from 55 to 65 petals; arranged regularly.
*Form.*—Very full-cupped at first; becoming cupped; petals being at first tightly cupped; becoming later loosely rolled outward at maturity.
Petals: Medium thickness; with inside velvety and outside satiny. Shape—outer—obovate; apex irregular, and sometimes with 1 notch, sometimes flat, and sometimes with a small point. Intermediate—obovate; apex irregular. Inner—obovate, apex irregular, though most have a small point.

This description of a newly opened flower was made from a rose grown in a greenhouse in the month of March, at West Grove, Pennsylvania, U. S. A.:

*Color.*—Outer petal: outside surface—Mallow Purple, Plate XII, with Light Lumiere Green, Plate XVII at base; inside surface—Rhodamine Purple, Plate XII, shading to Light Mallow Purple, Plate XII at outer edges, with Chartreuse Yellow, Plate XXXII at base. Intermediate petal: outside surface—Mallow Purple, Plate XII, with Pale Veronese Green, Plate XVIII at base; inside surface—Rhodamine Purple, Plate XII, with outer edge Mallow Purple, Plate XII, and Pale Veronese Green, Plate XVIII at base. Inner petal: outside surface—Mallow Purple, Plate XII, shading to Light Mallow Purple, Plate XII at center, with Sea Foam Green, Plate XXXI at base; inside surface—Tyrian Rose, Plate XII, with Rhodamine Purple, Plate XII at tip, and Chartreuse Yellow, Plate XXXI at base.

This description was made from a rose that was open for three days in a greenhouse in the month of March, at West Grove, Pennsylvania, U. S. A.:

*Color.*—Outer petal—outside surface—Mallow Purple, Plate XII, shading to Mallow Pink, Plate XII and then to white at base; edged with a narrow border of Tyrian Rose, Plate XII. Inside surface—Rhodamine Purple, Plate XII at outer edge, shading to Light Mallow Purple, Plate XII, and then to white at base. Inner petal: outside surface—Rose Color, Plate XII, shading to Deep Rose, Plate XII and then to Light Rose Pink, Plate XII; inside surface—Rhodamine Purple, Plate XII, shading to Light Mallow Purple, Plate XII, with Chartreuse Yellow, Plate XXXI at base.

*General color effect.*—Newly opened flower—between Rhodamine Purple, Plate XII and Tyrian Rose, Plate XII. 3-days open—Uniformly Rhodamine Purple, Plate XII.

*Behavior.*—Persist; fading purple.

*Flower longevity.*—On bush in greenhouse—10 days in March. Cut roses grown in greenhouse and kept at living-room temperatures—5 days in April.

*Reproductive organs*

Stamens: Medium number; arranged irregularly about pistils; mixed with petaloids.

Filaments: Few without anthers; medium length; whitish-yellow color.

Anthers: All open at once; medium size; occasionally an anther fused with a petaloid. Color—yellow.

Pollen: Moderate. Color—gold.

Pistils: Medium number.

Styles: Uneven; medium length; medium caliper; bunched.

Stigma: Color—pale yellow.

Ovaries: All enclosed in calyx.

Hips: None set.

Sepals: Permanent; medium length; spear-shaped.

Seeds: None.

*Plant*

Foliage:

*Leaves.*—Compound of 7 leaflets; normal abundance; medium size; moderately heavy.

*Leaflets.*—Shape—ovoid, with acute apex and round base. Margin—simply serrate.

*Color.*—Mature: upper surface—Varley's

Green, Plate XVIII; under surface—Chromium Green, Plate XXXII. Young: upper surface—Grass Green, Plate VI; under surface—Light Cress Green, Plate XXXI, with a slight underlying suffusion of bronze.

*Rachis (the supporting stem of the compound leaf).*—Medium caliper. Upper side—grooved; prickly. Under side—sparsely thorny.

*Stipules.*—Medium-long; narrow; with moderately long points turning out at an angle of 45°.

*Disease.*—Resistant to mildew and blackspot, as determined from comparison with other varieties grown under comparable cultural conditions at West Grove, Pennsylvania, U. S. A.

Growth:

*Habit.*—Bushy; upright; much-branched.

*Growth.*—Free.

*Canes.*—Medium caliper.

*Main stems.*—Color—bright green. Thorns—few; medium length; straight; with oval base. Prickles—none. Hairs—none.

*Branches.*—Color—bright green. Thorns—few; medium length; straight; with medium length, oval base. Prickles—none. Hairs—none.

*New shoots.*—Color—bronze. Thorns—few; medium length; straight; with medium length, oval base. Prickles—none. Hairs—none.

I claim:

A new and distinct variety of rose plant of the miniature class, substantially as herein shown and described, characterized particularly as to novelty by its true miniature habit of growth, and by the bright pink general color tonality of its flowers.

No references cited.